(12) United States Patent
Yaguchi et al.

(10) Patent No.: US 7,622,714 B2
(45) Date of Patent: Nov. 24, 2009

(54) STANDARD SPECIMEN FOR A CHARGED PARTICLE BEAM APPARATUS, SPECIMEN PREPARATION METHOD THEREOF, AND CHARGED PARTICLE BEAM APPARATUS

(75) Inventors: Toshie Yaguchi, Omitama (JP); Takeo Kamino, Hitachinaka (JP); Yoshifumi Taniguchi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 307 days.

(21) Appl. No.: 11/717,094

(22) Filed: Mar. 13, 2007

(65) Prior Publication Data
US 2008/0073521 A1    Mar. 27, 2008

(30) Foreign Application Priority Data
Mar. 14, 2006  (JP)  ............... 2006-068471

(51) Int. Cl.
*H01J 37/26* (2006.01)
*G01N 1/28* (2006.01)
*G01D 18/00* (2006.01)

(52) U.S. Cl. ............... 250/311; 250/252.1
(58) Field of Classification Search ............ 250/307, 250/310, 311, 252.1
See application file for complete search history.

(56) References Cited

U.S. PATENT DOCUMENTS 6,750,447 B2 *  6/2004  Houge et al. ............ 250/252.1
6,875,982 B2 *  4/2005  Bedell et al. ............ 250/307

FOREIGN PATENT DOCUMENTS

| JP | 7-71947 | 3/1995 |
| JP | 8-31363 | 2/1996 |
| JP | 2003-279321 | 10/2003 |

OTHER PUBLICATIONS

Nakayama, "Inspection and Measurement of ULSI Pattern by Electron-Beam System", The Journal of the Japan Society for Precision Engineering, 2002, pp. 342-344, vol. 68, No. 3. (Relevant Portions translated).

Misumi, et al., "Uncertainty in pitch measurements of one-dimensional grating standards using a nanometrological atomic force microscope", Measurement Science and Technology, 2003, pp. 463-471, vol. 14, Institute of Physics Publishing Ltd., UK.

"MAG*I*CAL® TEM Calibration Specimen: Certificate of Traceability", Structure Probe, Inc. Supplies, 2006, <http://www.2spi.com/catalog/standards/magical_cert_trace.html>.

* cited by examiner

*Primary Examiner*—Jack I Berman
(74) *Attorney, Agent, or Firm*—McDermott Will & Emery LLP (57) ABSTRACT

An object of the present invention is to provide a standard specimen for a charged particle beam enabling highly precise measurement of sub-micron to several 10 µm in size on an image and an apparatus using the standard specimen. In order to attain the above described object, the present invention provides a standard specimen for a charged particle beam including two different specimens for magnification or measurement calibration and a charged particle beam apparatus using the specimens.

15 Claims, 13 Drawing Sheets

STANDARD SPECIMEN FOR A CHARGED PARTICLE BEAM APPARATUS, SPECIMEN PREPARATION METHOD THEREOF, AND CHARGED PARTICLE BEAM APPARATUS

BACKGROUND OF THE INVENTION

1. Field of the Invention

The present invention relates to a standard specimen for a charged particle beam apparatus and relates in particular, in the occasion of carrying out length measurement of a specimen to be observed with an electron microscope, to a standard specimen for electron microscope measurement calibration enabling measurement of several ten μm or smaller micro size with high precision and a method for preparation thereof.

2. Description of Related Art

A scanning electron microscope is an apparatus of magnifying the specimen shape in an order of several hundred to several tens of million to form an image. In order to carry out precise calibration of magnification and length measured value of an image, for example, in the case of a Scanning Electron Microscope (SEM), a micro scale being a standard specimen having a pitch pattern, a size of which is known, is used to calibrate measurement in magnification in an order of fifty thousand-fold to several hundreds of thousand-fold. With respect to a specimen for measurement calibration of a scanning electron microscope, an example of length measurement calibrating member is described in JP-A-7-071947. In addition, an example of measurement calibrating specimen is described in JP-A-8-031363, Yoshinori Nakayama "Semiconductor Pattern Metrology with Electron Beam", The Journal of the Japan Society for Precision Engineering, Vol. 68, No. 3, 2002 and I Misumi, et al. "Uncertainty in pitch measurements of one-dimensional grating standards using a nanometrogical atomic force microscope", Meas. Sci. Technol. 14 (2003) 463-471. Moreover, an example of nanometrological calibration secondary standard specimen is described in JP-A-2003-279321.

On the other hand, in the case of a transmission electron microscope (TEM) and a scanning transmission electron microscope (STEM) carrying out observation with electrons transmitting a specimen, sizes on necessary sites are measured with the crystal lattice image, a size of which is already known, as a standard in magnification of several million-folds or more. A standard specimen for such an object, which is provided with a multi-layer film of Ge on a Si substrate and is prepared with an ion thinning method, is put on the market by Norrox Scientific Ltd (CANADA).

The measurement calibrating calibration member for a scanning electron microscope disclosed in the above described patent documents is not a film specimen for an electron beam to transmit and is not applicable for measurement calibration of (Transmission Electron Microscope: TEM) and Scanning Transmission Electron Microscope: STEM carrying out observation with electrons having transmitted the specimen.

In the case of the prior arts to carry out image observation utilizing the above described other transmission electrons, in order to observe crystal lattice images between 0.2 nm and 0.3 nm such as metal, it is necessary to set a TEM to provide 0.3 million-fold magnification, to set a TV camera to provide approximately ten-fold magnification and lastly to provide not less than three million-fold magnification. In addition, in the case of a STEM, it is necessary to set magnification of three million-fold or more. Therefore, in the case of magnification of not more than several million-folds allowing observation of no lattice image, a structure to be observed undergoes length measurement with a lattice image as a standard to provide magnification three million-fold or more. Then secondary length measurement is carried out with the structure as a standard. However, the above described structure to be observed does not always fall in the desired region for observation. In such a case, there is no means for precise magnification and length measurement value calibration on images.

In addition, a standard specimen of the above described prior arts is prepared by the ion thinning method to prepare thin film by applying $Ar^+$ ion beam with several nm diameter.

In that case, a wide region undergoes thin-filming to give rise to deflection frequently. Therefore it is difficult to measure line width of multilayer film to become a precise standard.

SUMMARY OF THE INVENTION

An object of the present invention is to provide a standard specimen for a charged particle beam enabling highly precise measurement of sub-micron to several 10 μm in size on an image and an apparatus using the standard specimen in the case of a TEM, STEM or SEM carrying out observation with electrons transmitting a specimen.

In order to attain the above described object, the present invention provides a standard specimen for a charged particle beam including two different specimens for magnification or measurement calibration and a charged particle beam apparatus using the specimens.

According to the present invention, a Transmission Electron Microscope (TEM), a Scanning Transmission Electron Microscope (STEM) or a Scanning Electron Microscope (SEM) carrying out observation with electron transmitting a specimen enables highly precise measurement of sub-micron to several 10 μm in size on an image.

Other objects, features and advantages of the invention will become apparent from the following description of the embodiments of the invention taken in conjunction with the accompanying drawings.

DESCRIPTION OF THE INVENTION

Figure 1:
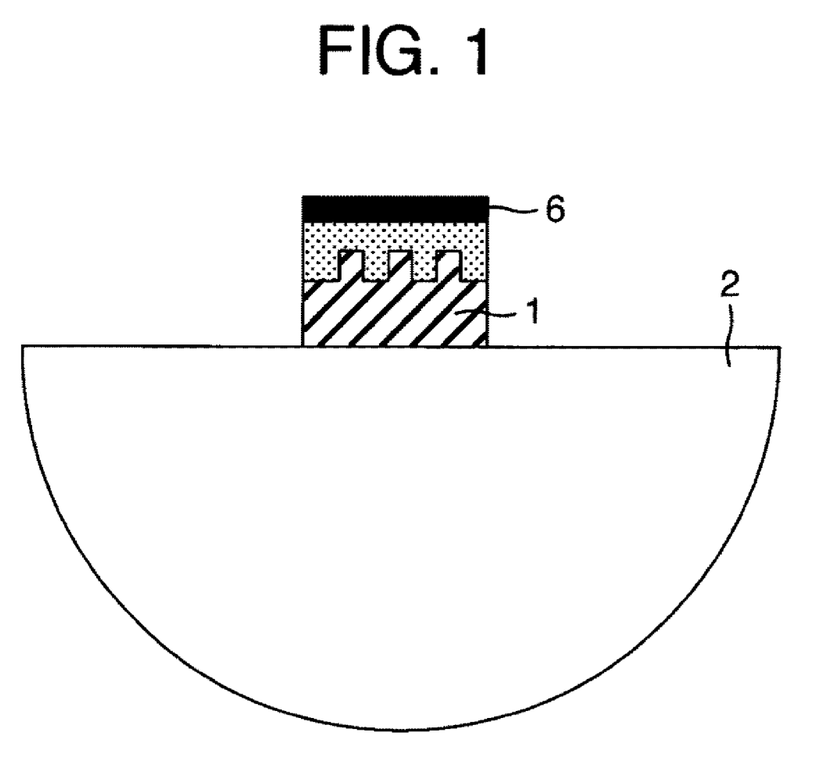
FIG. 1 describes an example of a standard specimen for measurement calibration of a scanning electron microscope.

FIG. 1 illustrates an embodiment of a standard specimen for an Electron Microscope measurement calibration being an embodiment of the present invention. A specimen for measurement calibration is a sectional film specimen 1 (first standard specimen) of a line and space pattern disposed on a Si [110] substrate. The groove portion between lines is embedded with organic material (second standard specimen). That is, two specimens are engaged in a complex state.

A specimen piece has a thickness of around 0.1 μm. Observing the piece in high magnification, a crystal lattice image of 0.3135 nm Si (111) can be observed with a TEM or a STEM. The sectional film specimen 1 is fixed on a half-disc specimen carrier 2 of 3 mm diameter. Tungsten protecting film 6 adheres to the uppermost surface of the sectional specimen piece for beam damage prevention at the time of processing the sectional plane by a Focused Ion Beam (FIB) 8. Film-thinning process is carried out in an orientation perpendicular to the arrangement direction so that an arrangement of arranged patterns is left.

A pitch measurement of the line and space of Si is measured and compared with a nominal value. Then magnification is calibrated. Otherwise, in stead of bringing the above described nominal value into comparison, the pitch measurement having been calibrated in advance in a lattice plane-to-plane distance can be brought into comparison to calibrate magnification. For three million-fold or more magnification, Si lattice image is observed directly for magnification calibration with the Si (111) lattice plane-to-plane distance being 0.3135 nm as a standard. In three million-fold or less magnification, measuring the pitch measurements at a plurality of points, the average value thereof is used for magnification calibration.

Figure 2A:
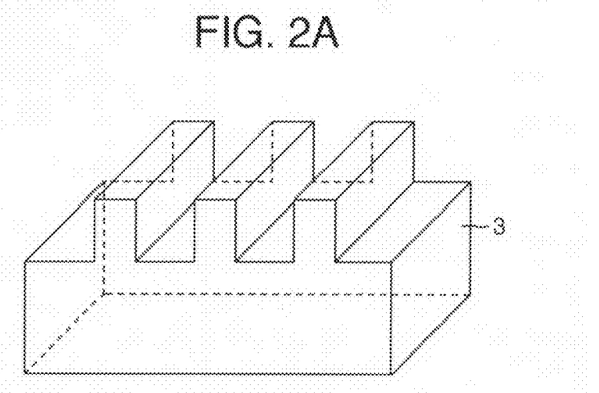
FIGS. 2A to 2C describes an example of a standard micro scale.
Figure 2B:
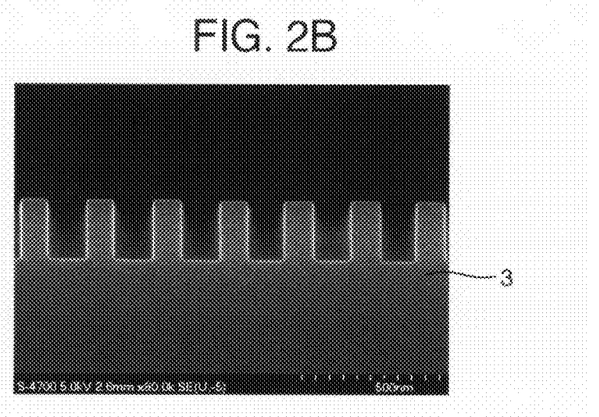
Figure 2C:
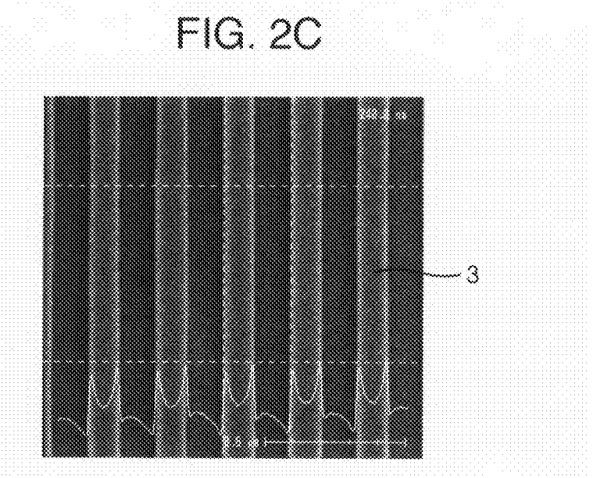

FIGS. 2A, 2B and 2C illustrate an appearance diagram, a sectional SEM image and a top side SEM image respectively of a standard micro scale 3 used for the present invention. A line and space pattern is arranged in a Si chip in a 240 nm uniform distance. The actual chip size is 4 mm±0.2 nm×4 mm±0.2 nm.

Figure 3A:
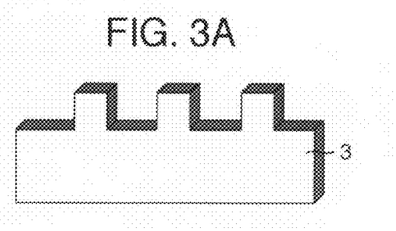
FIGS. 3A to 3E describes an example of a specimen preparation procedure.
Figure 3B:
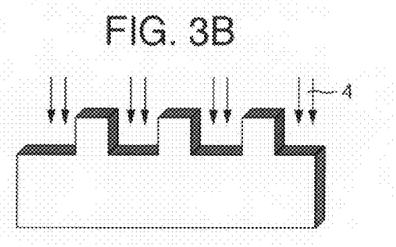
Figure 3C:
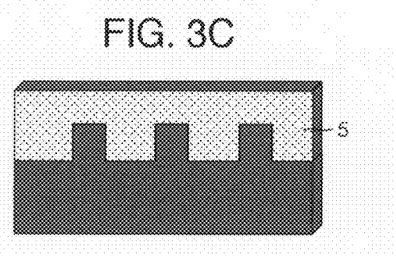
Figure 3D:
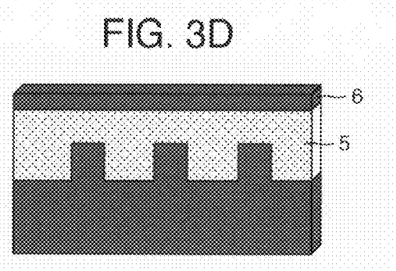
Figure 3E:
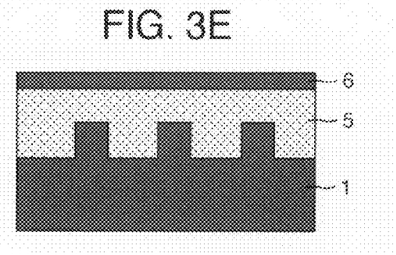
Figure 4A:
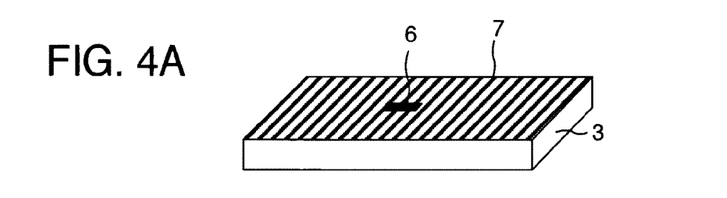
FIGS. 4A to 4E describes an example of a specimen preparation procedure (Part 1)
Figure 4B:
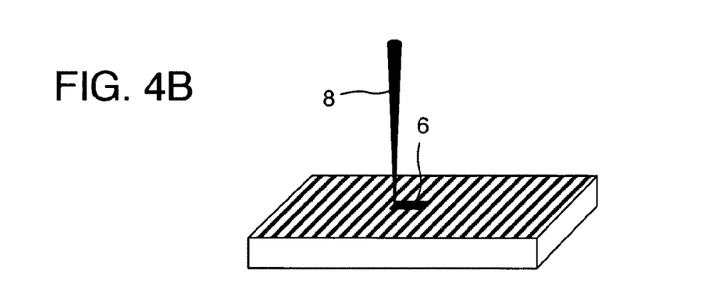
Figure 4C:
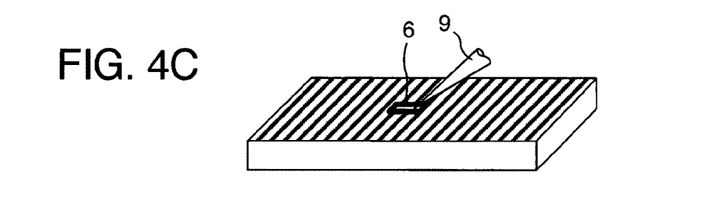
Figure 4D:
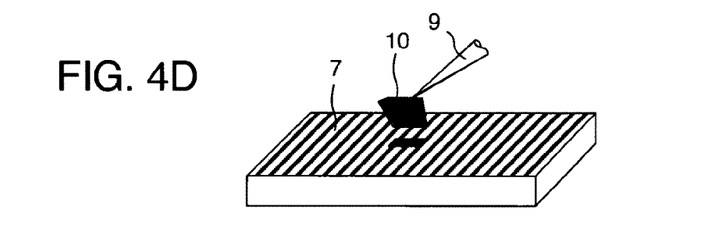
Figure 4E:
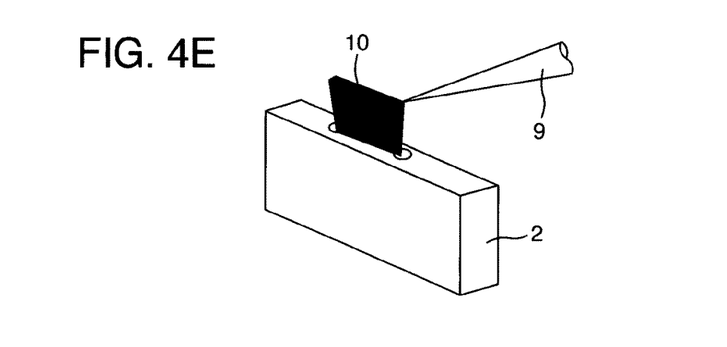

FIGS. 3A to 3E illustrates a specimen preparation procedure of the present embodiment. In order to retain the line and space pattern at the time of preparing sectional film from the standard micro scale 3 illustrated in FIGS. 2A to 2C, carbon protection film 5 is prepared (FIG. 3C) on the surface having the line and space pattern of the standard micro scale 3 (FIG. 3A) by CVD 4, carbon evaporation or application of carbon solution (FIG. 3B). Next, in order to prevent the carbon protection film 5 from sputtering at the time of FIB processing for film specimen preparation further, tungsten protection film 6 with slow sputtering speed is prepared by FIB assisted deposition (FIG. 3D). Thereafter, film-thinning process is carried out with the FIB 8 (FIG. 3E). In these steps, when preparing the film specimen from the chip, the steps up to the step of FIG. 3C can be carried out with a 4 mm×4 mm chip. Then dicing saw and the like can be employed to cut out a 1 mm×1.5 mm×50 μm thickness fine-chip, and the chip can be fixed onto a 3 mm diameter half-disc specimen carrier 2 with adhesives or the like for the next steps of FIGS. 3D and 3E. Otherwise, completing up to the step of FIG. 3D, a fine specimen piece can be taken out with a FIB micro sampling method. FIGS. 4A to 4G illustrates a procedure of taking out a specimen piece with the FIB micro sampling method from the standard specimen chip 7 of the standard micro scale 3 with carbon protection film. At first, the standard specimen chip 7 with carbon protection film is set inside the FIB apparatus in advance. Then FIB assisted deposition attaches the tungsten protection film 6 to the standard specimen chip 7 (FIG. 4A). Next, leaving a part of the periphery thereof uncut, the chip 7 is processed with the FIB 8 (FIG. 4B). Next, a metal probe 9 is attached thereto by FIB assisted W deposition (FIG. 4C). Next, the uncut joint portion of the micro specimen piece 10 and the standard specimen chip 7 is split with the FIB 8 (FIG. 4D) and is fixed onto the half-disc specimen carrier 2 (FIG. 4E). The fixation is carried out by FIB assisted W deposition. Thereafter, the metal probe 9 is cut with the FIB 8 (FIG. 4F) and undergoes film-thinning processing with the FIB 8 (FIG. 4G). As a result, the sectional film specimen 1 illustrated in FIG. 1 is completed. FIGS. 5A and 5B illustrates a transmission image (FIG. 5A) of the film specimen 11 prepared by irradiating broad Ar ions with around 3 mm diameter not with the FIB method and a transmission image (FIG. 5B) of the film specimen 12 prepared with the FIB method. It is difficult for the method of the above described the step of FIG. 5A to control a specimen thickness and a certain region will result in several ten nm thickness. Then, strain 13 appearing in the photograph occurs. Therefore the pattern may give rise to stain as well. On the other hand, the FIB method enables observation of secondary electron image excited on the specimen surface with narrowly squeezed ion at the time of processing. Therefore, the thickness is controllable without difficult, scarcely giving rise to strain to the specimen.

Figure 6A:
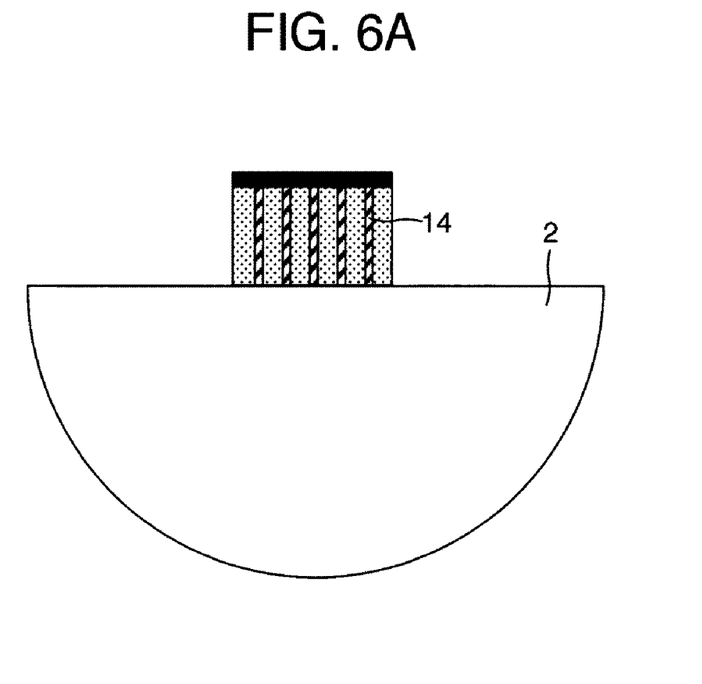
FIGS. 6A and 6B describes an example of flat film standard specimen with a standard specimen micro scale.
Figure 6B:
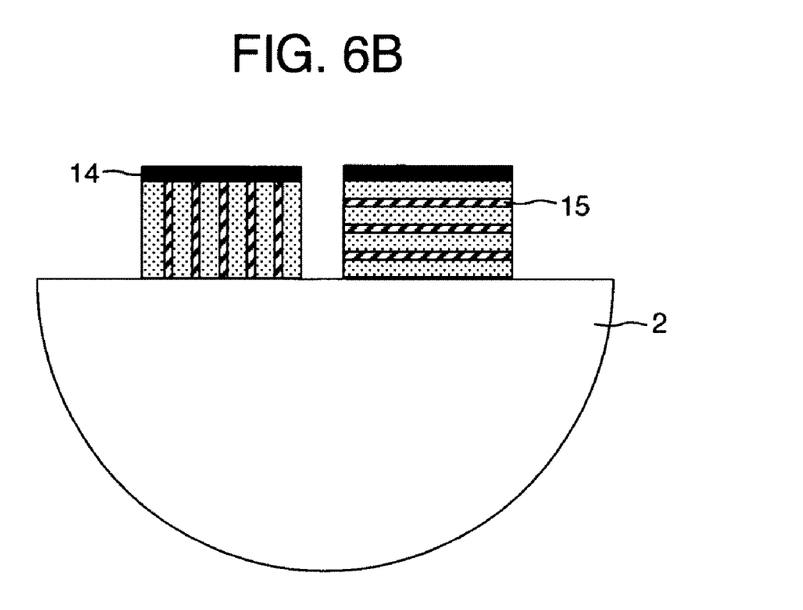

FIGS. 6A and 6B illustrates a plane standard specimen with a standard specimen micro scale. FIG. 6A illustrates an example of a horizontal magnification calibration flat film standard specimen 14 and FIG. 6B illustrates an example of installing a horizontal magnification calibration flat film standard specimen 14 and a vertical magnification calibration flat film standard specimen 15 on a same half-disc specimen carrier 2. Thereby, the both magnification calibration in different X/Y directions rotating the view is feasible.

Figure 7A:
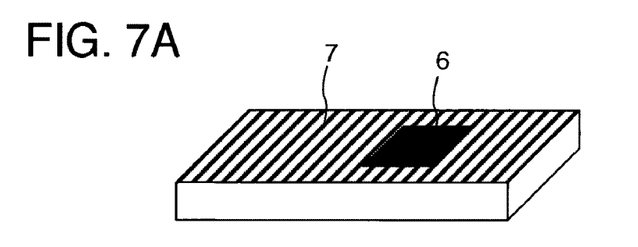
FIGS. 7A to 7D describes an example of a flat standard specimen preparation procedure (Part 1)
Figure 7B:
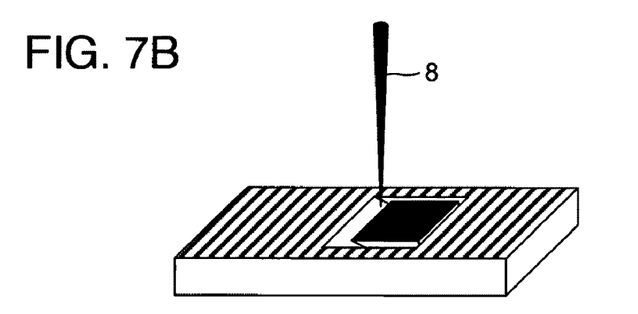
Figure 7C:
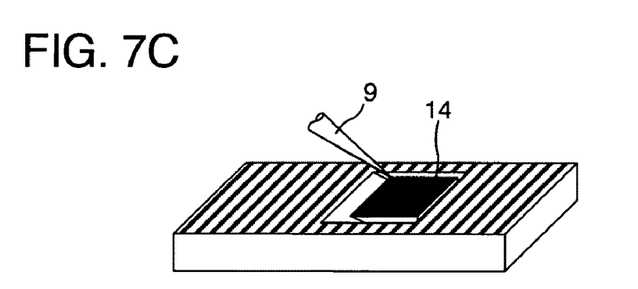
Figure 7D:
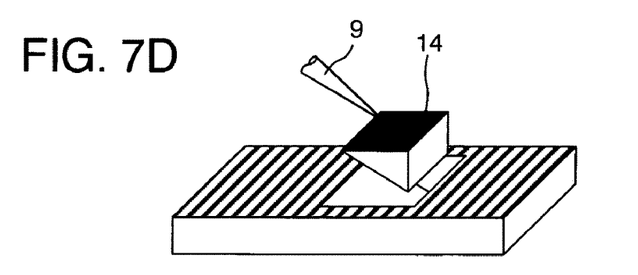
Figure 7E:
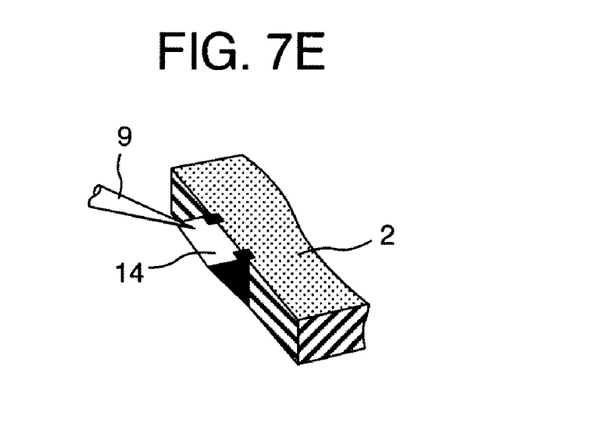
FIGS. 7E to 7G describes an example of a flat standard specimen preparation procedure (Part 2)
Figure 7F:
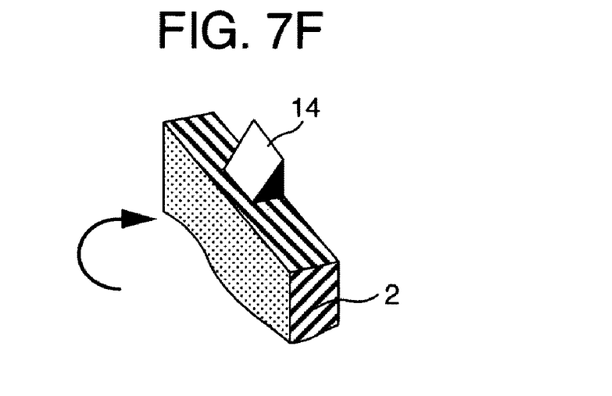
Figure 7G:
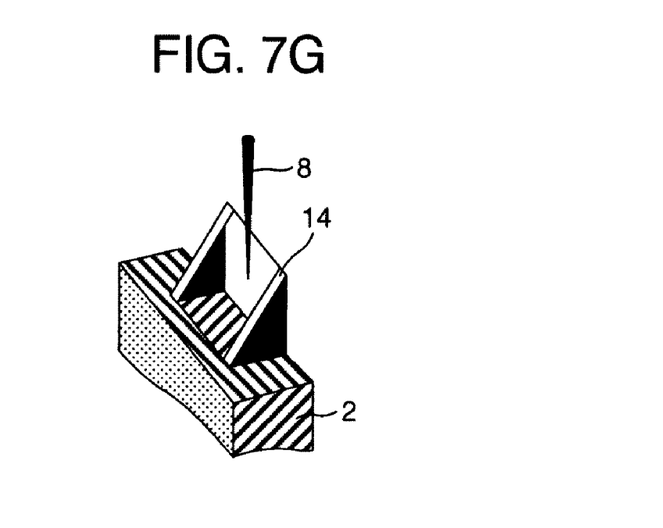
Figure 8A:
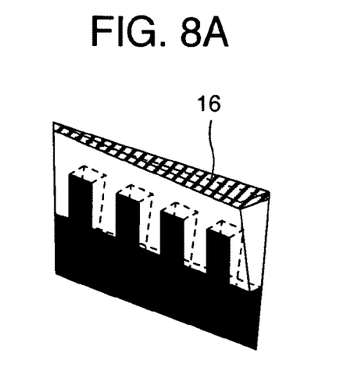
FIGS. 8A to 8D describes an example of a thin standard specimen.
Figure 8B:
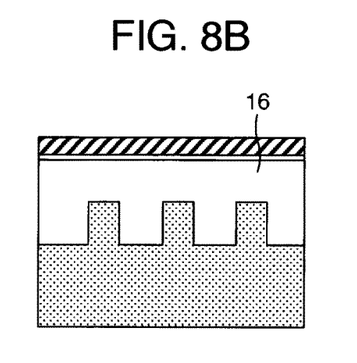
Figure 8C:
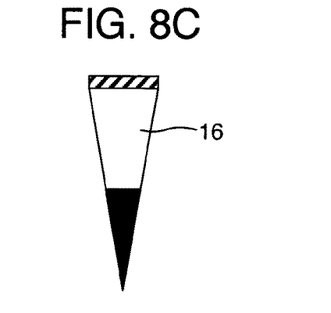
Figure 8D:
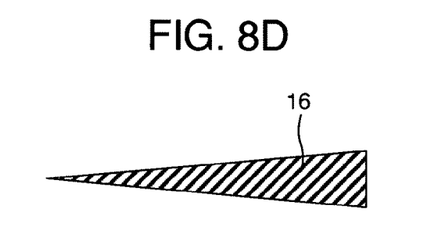
Figure 9A:
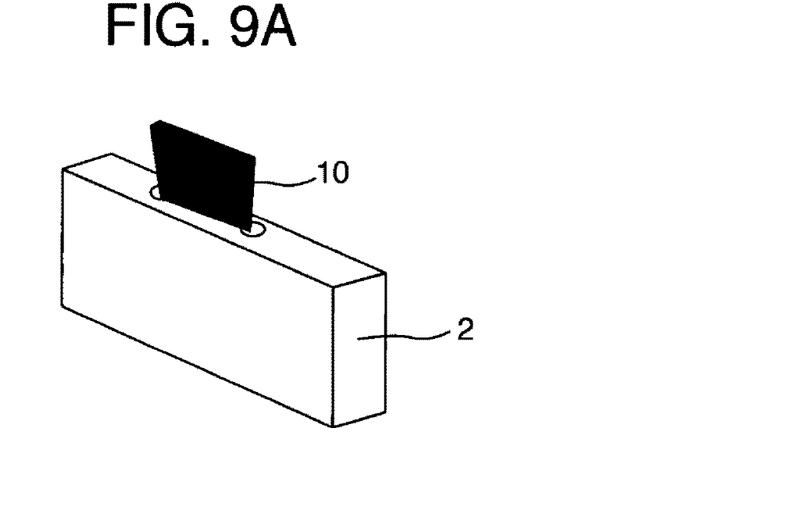
FIGS. 9A and 9B describes an example of sphenoid standard specimen preparation method.
Figure 9B:
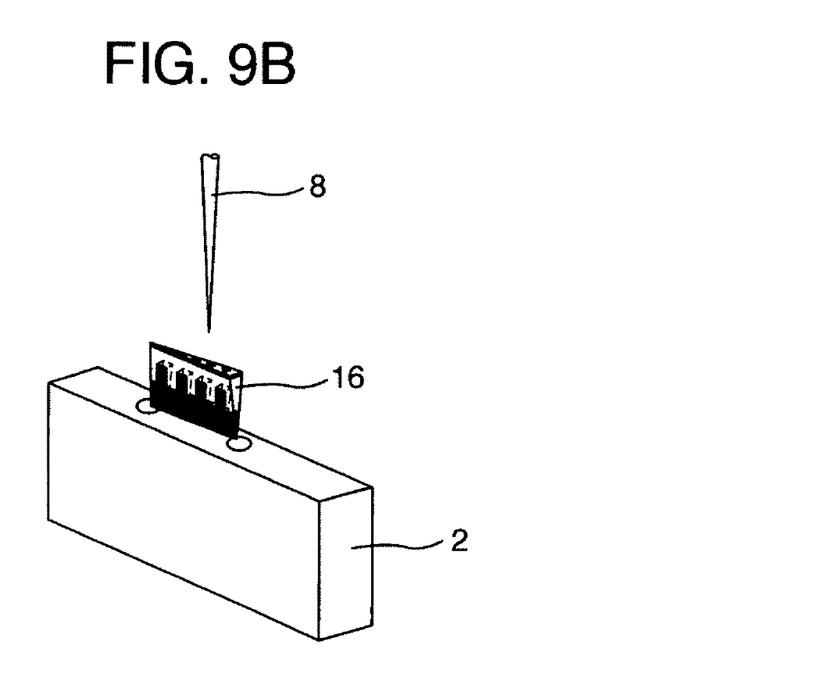

The pitch size is measured likewise the sectional standard specimen and compared with the nominal value. Then calibrate magnification is calibrated. Otherwise, the Si lattice image is observed in three million-fold or more magnification to measure length of a part of the pitch. Magnification calibration can be carried out based on that value. FIGS. 7A to 7G illustrates a procedure of taking out a specimen piece with the FIB micro sampling method from the standard specimen chip 7 to prepare vertical magnification calibration flat film standard specimen 15 in the horizontal direction. At first, the standard specimen chip 7 of with carbon protection film is set inside the FIB apparatus in advance. Then FIB assisted deposition adheres the tungsten protection film 6 to the standard specimen chip 7 (FIG. 7A). Next, leaving a part of the periphery thereof uncut, the chip 7 is processed with the FIB 8 except a part (FIG. 7B). Next, a metal probe 9 is attached thereto by FIB assisted W deposition (FIG. 7C). Next, the horizontal magnification calibration flat film standard specimen 14 and the uncut joint portion of the chip are cut off with the FIB 8 (FIG. 7D) and are fixed onto the half-disc specimen carrier 2 (FIG. 7E). The fixation is carried out by FIB assisted W deposition. Thereafter, the metal probe 9 is cut with the FIB 8 and is inclined by 90 degrees together with the half-disc specimen carrier 2 (FIG. 7F). Then the probe 9 undergoes film-thinning processing with the FIB 8 (FIG. 7G) so that the tungsten protection film 6 adhered at the step of FIG. 7A be eliminated. Thereby the vertical magnification calibration flat film standard specimen 15 in FIG. 6A is completed. In FIG. 7A, the direction of the specimen is rotated by 90 degrees. Then film specimen is prepared in the same procedure. Fixing the specimen beside the specimen in the step of FIG. 6A, FIG. 6B is completed. FIGS. 8A to 8D illustrates a perspective view (FIG. 8A), side view (FIG. 8B and FIG. 8C) and a top view (FIG. 8D) of a sphenoid standard specimen 16 being another embodiment of film standard specimen with a standard micro scale 3. The film standard specimen illustrated in FIG. 1 and FIGS. 7A to 7G has a uniform thickness. However, giving a sphenoid shape, a specimen can be provided with a different thickness. Thereby, it is possible to obtain a vision enabling image observation with contrast optimum to various types of observation conditions of TEM observation or STEM observation with low magnification to high magnification. In general, with low accelerating voltage, contrast is observed to be high. However, due to low transmission capability, thin specimen is suitable. In the case of high accelerating voltage with too thin specimen, contrast is not so intensive. In addition, in the case where the specimen thickness is not more than 0.1 µm, observation with three million-fold or more magnification enables observation of a crystal lattice image with lattice plane-to-plane distance 0.3135 nm of Si (111), for example. Therefore, it is possible to calibrate magnification based on that the lattice plane-to-plane distance of Si (111), for example. Accordingly, providing the standard specimen with thickness difference linearly, it is possible to provided optimum observation view without exception. FIGS. 9A and 9B illustrates a method of preparing a sphenoid standard specimen 16.

Figure 4F:
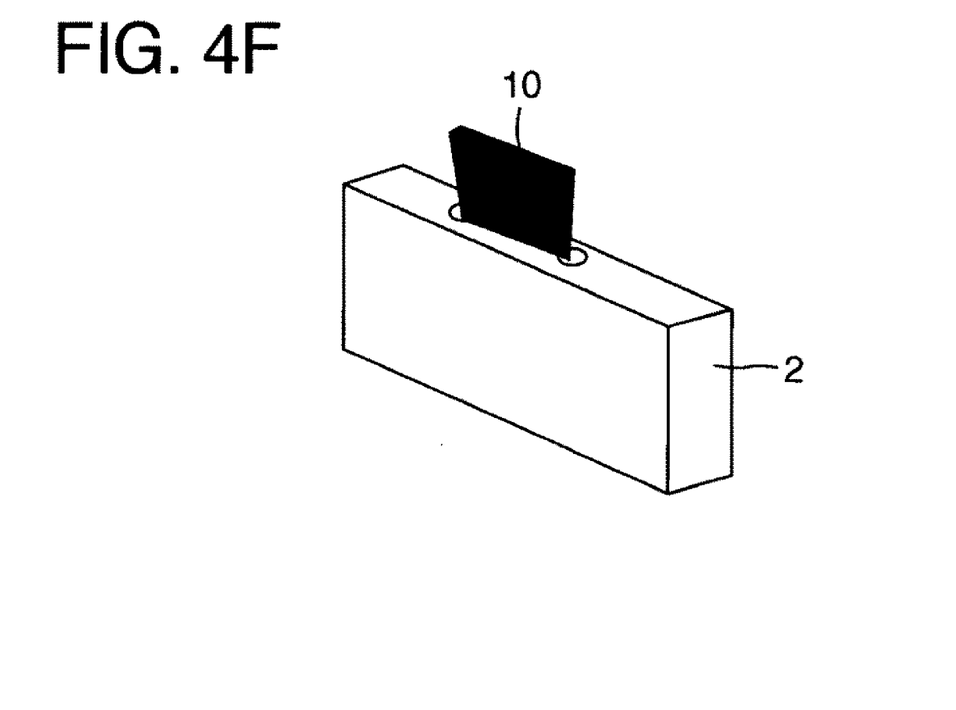
FIGS. 4F and 4G describes an example of a specimen preparation procedure (Part 2)
Figure 4G:
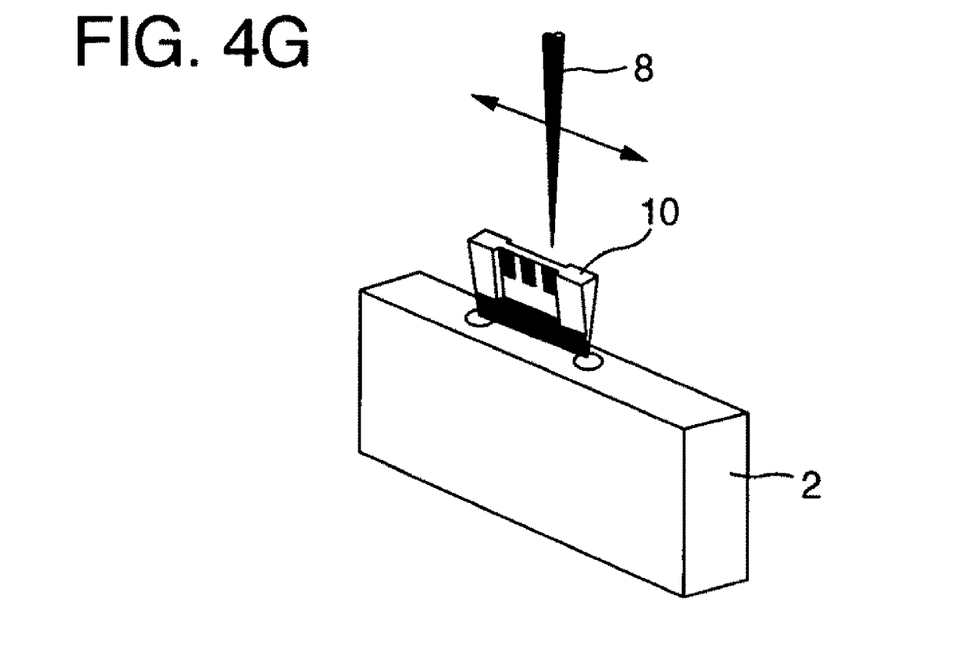
Figure 5A:
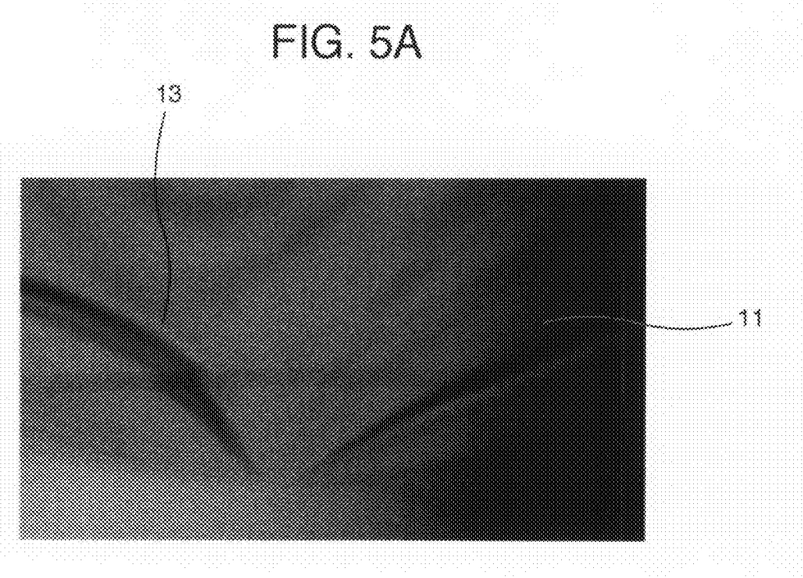
FIGS. 5A and 5B describes an example of transmitted image of a film specimen.
Figure 5B:
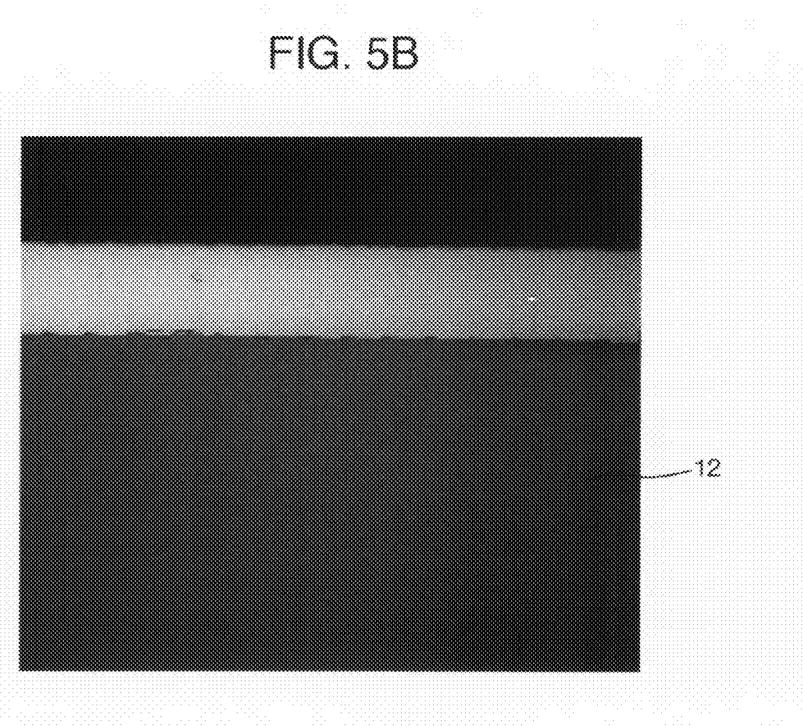

In the state (FIG. 9A) in FIG. 4F and FIG. 7F, the scanning of the FIB 8 is orientated not parallel along the specimen but is provided with an angle of around 1° to 2° to prepare the sphenoid standard specimen 16 (FIG. 9B). Also in the case of preparing a sphenoid specimen, the whole specimen piece does not undergo processing to provide sphenoid shape but undergoes sphenoid processing with a part being left. Thereby it is possible to prevent strain.

Figure 10:
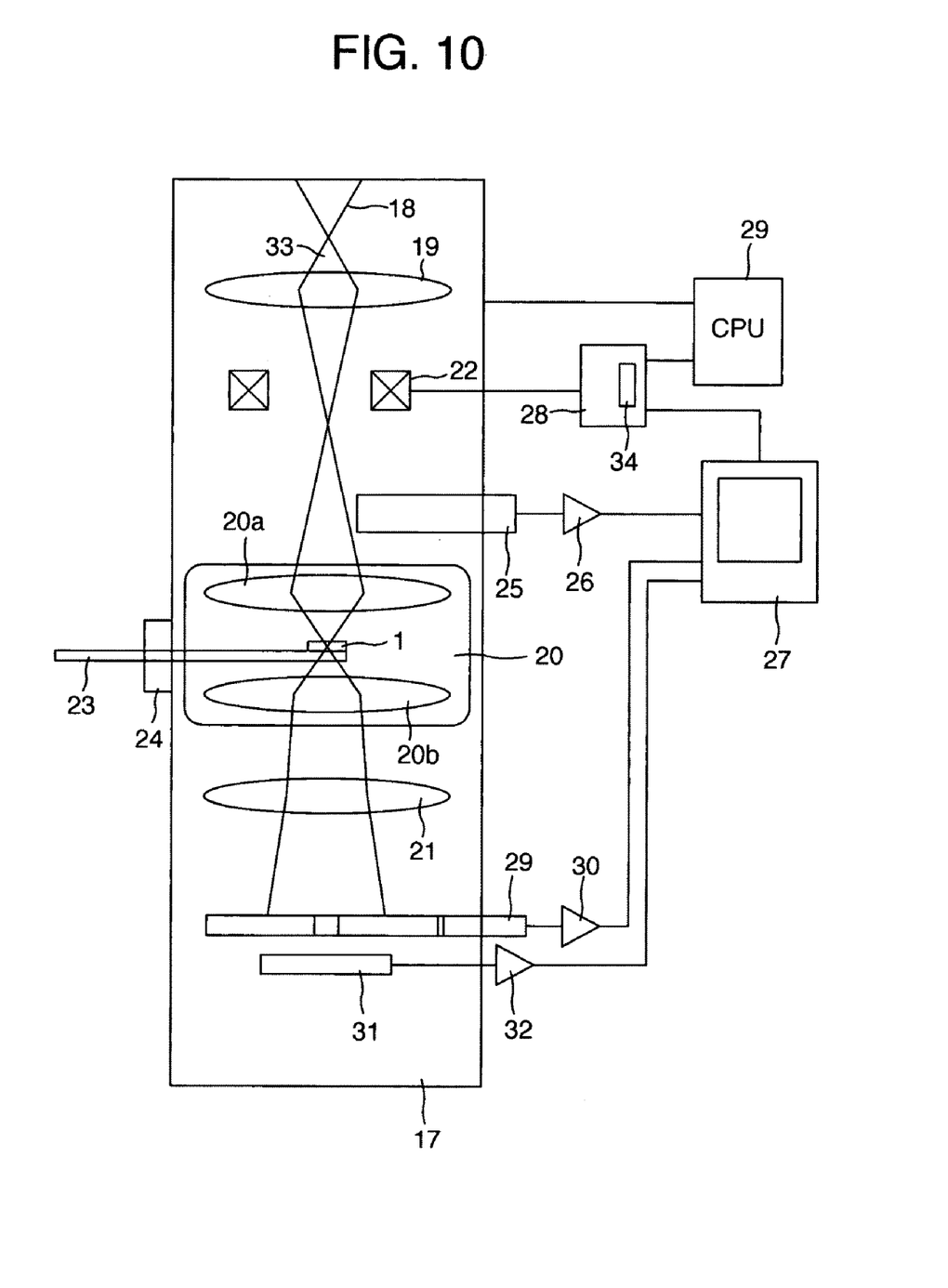
FIG. 10 describes an example of a Scanning Transmission Electron Microscope.

FIG. 10 illustrates a block diagram of a Scanning Transmission Electron Microscope 17 for magnification calibration with the present invention. The mirror of the Scanning Transmission Electron Microscope 17 comprises an electron gun 18, a condenser lens 19, an objective lens 20 and a projector lens 21. The object lens 20 is provided with two lens functions of a pre-magnetic field 20a and a pro-magnetic field 20b with ferromagnetization. A scanning coil 22 is disposed between the condenser lens 19 and the objective lens 20. A sectional film specimen 1 is inserted between the premagnetic field 20a and the promagnetic field 20b of the objective lens 20. The section film specimen 1 is mounted onto a specimen holder 23. The specimen holder 23 is moved with a specimen micro motion apparatus 24. The present example will be described in the case where electron beam irradiation for measurement calibration or magnification calibration is carried out in the state where a standard specimen is placed on the specimen micro motion apparatus 24 but will not be limited thereto. Another placing carrier instead of the specimen micro motion apparatus 24 can be provided to place a standard specimen. In the present example will be described the case of carrying out measurement calibration. But magnification calibration can be carried out with the same principle.

A secondary electron detector 25 is incorporated above the sectional film specimen 1 and under the scanning coil 22. The secondary electron detector 25 is connected to the scanning image displaying apparatus 27 through a signal amplifier 26. A scanning power supply 28 is connected to the scanning coil 22. The scanning power supply 28 is connected to the scanning image displaying apparatus 27 and Scanning Transmission Electron Microscope CPU 29. The CPU 29 for observing a dark vision STEM image is arranged below the projector lens 21. The CPU 29 is connected to the scanning image displaying apparatus 27 through the signal amplifier 30. A bright vision STEM image detector 31 enabling entrance into and exit out of optical axis is provided below the CPU 9, which is connected to the scanning image displaying apparatus 27 through the signal amplifier 32.

Figure 11A:
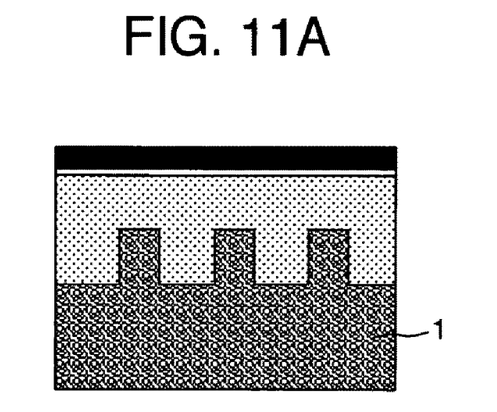
FIGS. 11A to 11C describes an example of high-precision measurement metrology with a standard specimen.
Figure 11B:
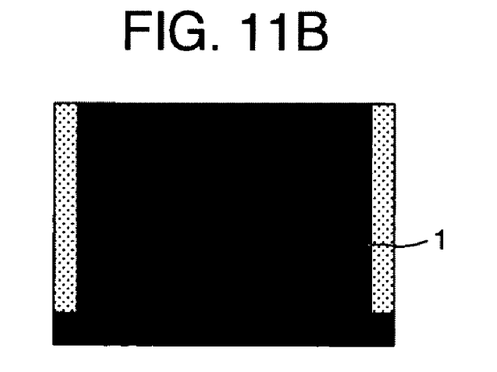
Figure 11C:
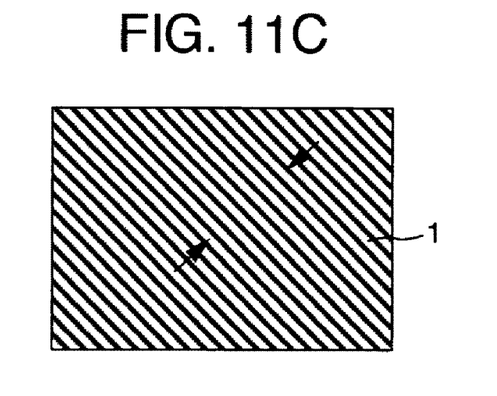

The electron beam 33 is converged in a spot shape on the section film specimen 1 with the premagnetic field 20a of the condenser lens 19 and the objective lens 20 to scan above the surface of the sectional film specimen 1 with the scanning coil 22. Sawtooth wave current flows in the scanning coil 22. The scanning width on the plane of the sectional film specimen 1 of a flux of the electron beam 33 is varied with the amount of that current. The synchronized sawtooth wave signal is also transmitted to a deflection coil of the scanning image displaying apparatus 27. The electron beam of the scanning image displaying apparatus 27 fully scans the respective scenes. In that occasion, with the scanning width being L, the magnification M of the operating electron microscope is equal to L/1. The secondary electron detector 25 is irradiated by the electron beam 33 to detect secondary electrons released from the sectional film specimen 1. The signal amplifier 26 amplified the signal thereof to modulate luminance of the scanning image displaying apparatus 27 with that signal. The bright vision STEM image detector 31 detects transmitted electrons scattered with the angle being half the angle from the sectional film specimen 1 within the range of approximately 50 mrad. The signal amplifier 32 amplifies that signal and modulates luminance of the scanning image displaying apparatus 27 with that signal. The CPU 29 is likewise as well. The electron beam 33 is irradiated to detect electrons (elastic scattering electrons) scattered with the scattering angle being half the angle from the sectional film specimen 1 within the range of approximately 80 mrad to 500 mrad. The signal amplifier 30 amplifies that signal and modulates luminance of the scanning image displaying apparatus 27 with that signal. In that case, the image provides contrast reflecting average atomic number of the sectional film specimen 1. Thereby the shape and the crystal structure of the sectional film specimen 1 are observed. Magnification M in the range between 1000-fold and 10 million-fold varies resistance value of the deflecting substrate 34 inside the scanning power supply 28 in 10000-fold, 0.1 million-fold and a million-fold respectively to vary the current flowing in the scanning coil 22. Therefore, difference in intrinsic resistance and difference in contact resistance and the like gives rise to difference in magnification precision in each range. Therefore, the necessity for carrying out magnification calibration in each range occurs. A high precision measurement metrological method of the sectional film specimen 1 is illustrated with FIGS. 11A to 11C. A standard specimen observation example is illustrated in the 0.1 million-fold range in FIG. 11A and in the million-fold range in FIGS. 11B and 11C respectively. In FIG. 11A, observation of two pitches of the sectional film specimen 1 is enabled. In FIG. 11B, observation of a line portion of a line and space forming a pitch is enabled. In FIG. 11C, observation of a Si lattice image of a standard specimen film portion is enabled. A size of the sectional film specimen 1 is determined with a Si lattice image of the standard specimen film portion, that is, a size of the region used for magnification calibration is determined. At first, ten crystal lattice images covering ten lines (arrowed portion) with Si (111) lattice plane-to-plane distance 0.3135 nm is measured so that the measured value is divided by 3.135 nm to derive actual magnification M2 and derive correction coefficient K=M2/(display magnification M1). In the million-fold range, display magnification is multiplied by the correction coefficient K, deriving the actual magnification. That magnification is applied to observation magnification illustrated in FIG. 11B. Thereby the calibration value of the line width in the line portion is measured. Next, dropping the observation magnification to 0.1 million-fold range, the calibration value of the line width measured in FIG. 11A is used to measure the actual magnification M2'. Next, from the display magnification M1', magnification correction coefficient K'=M2'/M1' in the 0.1 million-fold range in FIG. 11A is derived. Next, measuring the pitch in magnification so as to allow several pitches to enter to observe the same sites in the 10000-fold range, magnification correction coefficient is obtained.

So far, the present example was described by taking an Electron Microscope for detecting transmission electrons as an example. However the standard specimen having undergone complex of two specimens is applicable to a Scanning Transmission Electron Microscope as well.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A standard specimen for a charged particle beam used for magnification or measurement calibration of a charged particle beam apparatus, wherein:
the standard specimen is configured so that patterns arranged in a predetermined pitch are disposed on a material having a predetermined lattice structure, and
the standard specimen has undergone film-thinning processing so as to enable the charged particle beam to transmit.

2. The standard specimen for a charged particle beam according to claim 1, wherein the standard specimen has undergone film-thinning processing in a direction perpendicular to the direction of the arrangement of the patterns.

3. The standard specimen for a charged particle beam according to claim 1, wherein material having lattice structure is provided between lines of the arranged patterns.

4. The standard specimen for a charged particle beam according to claim 3, wherein the arranged patterns and the material including the lattice structure are configured to be engaged to each other.

5. The standard specimen for a charged particle beam according to claim 1, wherein the standard specimen is a magnification standard specimen including a pitch size (period) having known periodic structure as a nominal value.

6. The standard specimen for a charged particle beam according to claim 1, wherein the standard specimen is arranged so that a film plane is perpendicular to an optical axis of the charged particle beam.

7. The standard specimen for a charged particle beam according to claim 1, wherein the film-thinning processing of the standard specimen enables lattice observation with the charged particle beam.

8. The standard specimen for a charged particle beam according to claim 1, wherein a film plane of the standard specimen on which two different specimens which have undergone film-thinning processing are combined is orientated perpendicular to the charged particle beam.

9. A standard specimen for a charged particle beam used for magnification or measurement calibration of a charged particle beam apparatus, wherein:
the standard specimen is configured so that a material having a predetermined lattice structure is disposed between patterns arranged in a predetermined pitch, and
the standard specimen has undergone film-thinning processing so as to enable the charged particle beam to transmit.

10. The standard specimen for a charged particle beam according to claim 9, wherein the standard specimen has undergone film-thinning processing in a direction perpendicular to the direction of the arrangement of the patterns.

11. The standard specimen for a charged particle beam according to claim 9, wherein the arranged patterns and the material including the lattice structure are configured to be engaged to each other.

12. The standard specimen for a charged particle beam according to claim 9, wherein the standard specimen is a magnification standard specimen including a pitch size (period) having known periodic structure as a nominal value.

13. The standard specimen for a charged particle beam according to claim 9, wherein the standard specimen is arranged so that a film plane is perpendicular to an optical axis of the charged particle beam.

14. The standard specimen for a charged particle beam according to claim 9, wherein the film-thinning processing of the standard specimen enables lattice observation with the charged particle beam.

15. The standard specimen for a charged particle beam according to claim 14, wherein a film plane of the standard specimen on which two different specimens which have undergone film-thinning processing are combined is arranged so that the film plane is orientated perpendicular to the charged particle beam.

* * * * *